(12) United States Patent
Bernstein

(10) Patent No.: US 7,772,275 B2
(45) Date of Patent: *Aug. 10, 2010

(54) COMPOSITIONS AND METHOD FOR TREATING AFFECTIVE, PAINFUL OR ALLERGIC DISORDERS

(75) Inventor: Joel E. Bernstein, Deerfield, IL (US)

(73) Assignee: Gideon Pharmaceuticals, Inc., Vernon Hills, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/372,535

(22) Filed: Feb. 17, 2009

(65) Prior Publication Data

US 2009/0182034 A1   Jul. 16, 2009

Related U.S. Application Data

(60) Division of application No. 10/781,254, filed on Feb. 18, 2004, now Pat. No. 7,629,378, which is a continuation of application No. 10/294,409, filed on Nov. 14, 2002, now abandoned.

(51) Int. Cl.
*A61K 31/335* (2006.01)
(52) U.S. Cl. .................................... 514/450
(58) Field of Classification Search .................. 514/450
See application file for complete search history.

(56) References Cited

U.S. PATENT DOCUMENTS

| 4,370,324 A | 1/1983 | Bernstein |
| 4,395,420 A | 7/1983 | Bernstein |
| 4,505,909 A | 3/1985 | Bernstein |
| 4,636,125 A | 1/1987 | Burgard |
| 5,502,047 A | 3/1996 | Kavey |
| 6,096,738 A | 8/2000 | Bernstein |

7,629,378 B2 * 12/2009 Bernstein ................ 514/450

FOREIGN PATENT DOCUMENTS

| CA | 1177406 | 11/1984 |
| CA | 1185179 | 4/1985 |
| CA | 1198059 | 12/1985 |

OTHER PUBLICATIONS

Bogaert et al, "Plasma Levels of he Cis-andTrans-Isomers of Doxepin and Desmethyldoxepin after Administration of Doxepin to Patients," *Drug Res.*, 31 (1): 113-115 (1981).
Midha et al., "Stereoselective pharmacokinetics of doxepin isomers," *European Journal of Clinical Pharmacology*, 42 (5): 539-544 (1992) (Abstract).
Otsuki et al., "Comparison of Pharmacological Activities of Doxepin Hydrochloride with Its Geometrical Isomers," *Oyo Yakuri*, 6 (5): 973-984 (1972) (Abstract).
Pinder et al., "Doxepin Up-to-date: A Review of its Pharmacological Properties and Therapeutic Efficacy with Particular Reference to Depression," *Drugs*, 13: 161-218 (1977).
Ross, CRC Handbook of Stereoisomers: Drugs in Pharmacology, "*Antidepressant Drugs: (Z)- and (E)-Isomers*," CRC Press, Boca Raton, Fla., pp. 243-255 (1984).
USP25,2000, United States Pharmacopeia Convention, Inc., Rockville, Maryland, 25th Ed., Abstract p. 614 (2002).
Yan et al., "Absolute bioavailability an stereoselective pharmacokinetics of doxepin," *Xenobiotica*, 32 (7): 615-623 (2001).
International Search Report issued in PCT/US2003/36600 (2004).
Page 1 of Office Action issued in GB2411356 (2005).

* cited by examiner

*Primary Examiner*—Jennifer M Kim
(74) *Attorney, Agent, or Firm*—Barnes & Thornburg LLP; Alice O. Martin

(57) ABSTRACT

Therapeutic compositions of doxepin and having a preponderance of the cis doxepin isomer over the trans doxepin isomer provide therapeutic effects for affective, painful, or allergic disorders without the sedative effects commonly experienced with compositions having a preponderance of the trans doxepin isomer.

5 Claims, No Drawings

COMPOSITIONS AND METHOD FOR TREATING AFFECTIVE, PAINFUL OR ALLERGIC DISORDERS

CROSS-REFERENCE TO RELATED PATENT APPLICATIONS

This patent application is a divisional of U.S. application Ser. No. 10/781,254, filed Feb. 18, 2004, which is a continuation of U.S. application Ser. No. 10/294,409, filed Nov. 14, 2002, now abandoned, the contents of which applications are incorporated by reference in their entireties.

BACKGROUND

Doxepin hydrochloride is a tricyclic compound most frequently used to treat the affective disorders depression and anxiety, but also less commonly employed as a secondary or tertiary treatment modality for a variety of painful (e.g. headache and neuropathic pain) and allergic (e.g. urticaria disorders. While doxepin is generally recognized as effective for the treatment of such disorders, its use is limited by the system side effects associated with its ingestion or topical application. Principal among the systemic side effects accompanying doxepin administration, and most limiting to its usefulness as a drug, is sedation which occurs in from 20% to over 60% of subjects depending upon dosage and route of doxepin administration. According to U.S. Pat. No. 25,2000, United States Pharmacopeial Convention Inc., Rockville, Md. p. 614, doxepin hydrochloride U.S.P. is a geometric isomer mixture "containing not less than 13.6% and not more than 18.1 %" of this cis isomer and "not less than 81.4% and not more than 88.2%" of the trans isomer.

In an attempt to discover a compound that might have similar effectiveness to doxepin hydrochloride U.S.P. but less associated sedation, the applicant has evaluated the cis isomer, which as mentioned above constitutes less than 18.1 % of doxepin hydrochloride. Applicant has disocovered that cis doxepin hydrochloride, while purportedly more potent than doxepin hydrochloride U.S.P. in animals, quite surprisingly produces less sedation at therapeutically effective dosages. The invention includes pharmaceutical compositions of cis doxepin suitable for administration to patients with affective disorders, painful disorders, or allergic disorders.

DETAILED DESCRIPTION OF THE PREFERRED EMBODIMENT

In accordance with the invention, formulations are provided that incorporate a preponderance of the cis doxepin isomer over the trans isomer into pharmaceutically acceptable vehicles suitable for use in human patients. Such formulations include those for application to the skin, such as solutions, creams, ointments, gels, lotions, or pastes. Such formulation also include those for application to mucous membranes, including ophthalmic and nasal solutions and solutions and suspensions, suppositories, and plasticized formulations suitable for oral and vaginal applications. Cis doxepin may also be formulated in sterile solutions or suspensions suitable for intradermal, subcutaneous, intramuscular, intravenous, or cerebrospinal injection. In each of the foregoing formulations, whether for application to the skin, application to the mucous membranes, or for injection, the cis doxepin isomer may be present in the amount of about 0.01% to about 10% by weight, and preferably about 0.05% to about 5% by weight, and any trans doxepin isomer that may be present is in an amount less than that of the cis doxepin isomer.

Formulations within the scope of the invention also includes those suitable for oral administration such as capsules, tablets, or liquid solutions or suspensions. In such formulations, the cis doxepin isomer may be present in amounts of about 0.5-500.0 mg, and preferably about 1.0-50.0 mg, per tablet, capsule, or 5 ml dose of liquid solution or suspension; and any trans doxepin isomer that may be present is in an amount less than that of the cix doxepin isomer.

Suitable pharmaceutical vehicles for the cis doxepin formulations of the instant invention, whether for topical application to skin or mucous membrane, injection, or oral administration, and methods of preparing such formulations as are within the scope of the invention, will be readily apparent to and understood by those skilled in the art.

The instant invention also comprises the method of applying, instilling, injecting, ingesting, or inhaling medicinal formulations containing a preponderance of the cis doxepin isomer over the trans doxepin isomer in order to treat a wide range of affective, painful, and/or allergic disorders of man and animals such as depression, anxiety, migraine headache, tension headache, neuralgia, urticaria, allergic rhinitis, and pruritic disorders of the skin.

The compositions of the instant invention and the methods of their use will be more readily comprehended from the following examples.

EXAMPLES

The formulations used in the following examples were made using a cis doxepin composition prepared by Sigma Aldrich, Inc. of Sheboygan, Wis., the composition comprising not less than about 85% of the cis-isomer, with the balance of the composition being the trans-isomer. Amounts of cis doxepin as stated in the examples are the actual amounts of the cis doxepin isomer in each formulation.

Example 1

Cis doxepin isomer is incorporated into hard gelatin capsules in a dosage of 10 mg/capsule, and is administered once or twice daily to patients with acute or chronic urticaria in order to prevent new urticarial lesions.

Example 2

A cream containing cis doxepin isomer 1.0% by weight is applied two to four times daily to pruritic skin lesions by patients with atopic dermatitis. Application of this cream provides for relief of itching as well as more prompt resolution of the skin lesions without producing the incidence or severity of sedation observed with application of prior art doxepin containing creams in which the trans isomer is predominant.

Example 3

An aqueous solution of 0.2% by weight of the cis doxepin isomer is administered by nasal spray to the noses of patients with allergic rhinitis to treat and prevent nasal stuffiness.

Example 4

An aqueous solution of 0.1% by weight of the cis doxepin isomer is applied to the eyes of patients with allergic conjunctivitis to relieve symptoms of eye irritation.

Example 5

Suppositories containing 20 mg by weight of the cis doxepin isomer in a hydrogenated coglyceride base are inserted rectally twice to three times daily for relief of pain and/or itching in patients with proctitis or pruritis ani.

Example 6

Cis doxepin is incorporated into tablets containing 50 mg by weight of the cis doxepin isomer and such tablets are administered orally once to four times daily to patients with affective disorders so as to relieve feelings of depression or anxiety without producing substantial sedation in such patients.

While the foregoing is a description of the preferred embodiments of the instant invention it will be readily apparent to those skilled in the art that various modifications may be made therein without departing from the true scope and spirit of the invention as set forth in the appended claims.

I claim:

1. A method of treating affective, painful or allergic disorders in a subject in need thereof, the method comprising treatment with an effective amount of a composition containing a preponderance of cis doxepin isomer over trans doxepin isomer, said cis doxepin isomer being present in an amount of about 0.01% to about 10.0% by weight in a pharmaceutically acceptable vehicle, said composition being comparable in efficacy to compositions containing a preponderance of the trans doxepin isomer but with significantly less sedation and wherein the disorder is selected from the group consisting of atopic dermatitis, allergic rhinitis, and urticaria and the treatment is applying the composition to skin.

2. The method of claim 1 wherein said cis doxepin isomer is present in the amount of about 0.05-5.0% by weight.

3. A method of treating affective, painful, or allergic disorders by oral administration to a subject in need thereof and the treatment comprising an effective amount of a composition containing a preponderance of cis doxepin isomer over trans doxepin isomer, said cis doxepin isomer being present in an amount of about 0.5-500.0 mg per dose or 5 ml portion of liquid in a pharmaceutically acceptable vehicle, said composition being comparable in efficacy to compositions containing a preponderance of trans doxepin isomer but with significantly less sedative side effects and wherein the disorder is selected from the group consisting of atopic dermatitis and urticaria.

4. The method of claim 3 wherein said cis doxepin isomer is present in the amount of about 1.0-50.0 mg per dose.

5. A method of treating allergic conjunctivitis by applying to eyes an effective amount of a composition containing a preponderance of cis doxepin isomer over trans doxepin isomer, wherein said cis doxepin isomer is present in the amount of about 0.05-5.0% by weight.

* * * * *